United States Patent [19]

Di Virgilio et al.

[11] Patent Number: 5,474,890
[45] Date of Patent: Dec. 12, 1995

[54] METHOD FOR INDUCING THE ACROSOME REACTION IN HUMAN AND ANIMAL SPERMATOZOA

[76] Inventors: Francesco Di Virgilio, c/o Institute of General Pathology, Via Luigi Borsari, 46, I-44100 Ferrara; Carlo Foresta, c/o Institute of General Pathology, Via Trieste 75, I-35121 Padova, both of Italy

[21] Appl. No.: 138,715

[22] Filed: Oct. 18, 1993

Related U.S. Application Data

[63] Continuation of Ser. No. 865,605, Apr. 9, 1992, abandoned.

[51] Int. Cl.[6] .............................. A01N 1/02; G01N 33/48
[52] U.S. Cl. .................. 435/1.1; 435/4; 435/29; 436/906; 436/63
[58] Field of Search .................. 435/1, 17, 4, 29, 435/28, 975, 810; 436/906, 63

[56] References Cited

U.S. PATENT DOCUMENTS

| | | | |
|---|---|---|---|
| 4,036,212 | 7/1977 | Karuhn | 436/65 |
| 4,469,671 | 9/1984 | Zimmerman | 424/432 |
| 4,683,213 | 7/1987 | Ax | 436/63 |
| 4,767,703 | 8/1988 | Ax et al. | 435/4 |
| 4,945,044 | 7/1990 | Huszar | 435/17 |

OTHER PUBLICATIONS

Calamera et al; Andrologia; Jul.–Aug. 1987, 19 (14) pp. 460–463, Adenosine*5*triphosphate* (ATP) Content & Acrosin Activity in Polyzoospermic Subjects.

Calamera et al; "*ATP* Concentration & *Acrosin* Activity in Human Spermatozoa Their Relation with the Sperm Penetration Assay"; Andrologia; 18 (6). 1986. 574–580.

Foresta et al, "J. Bio Chem", vol. 267, No. 27, pp. 19443–19447, 1992.

Wong, P. V. D., "Br. J. Pharmacol", vol. 95, pp. 1315–1321, 1988.

Wassarman, Ann. Rev. Cell Biol., 3:109–142 (1987).

Dubyak, Am. J. Respir. Cell Mol. Biol., 4:295–300 (1991).

White et al., Biol. Reprod., 34:183–193 (1986).

Primary Examiner—Michael G. Wityshyn
Assistant Examiner—Louise N. Leary
Attorney, Agent, or Firm—Kirschstein, Ottinger, Israel & Schiffmiller

[57] ABSTRACT

A method for assessing the fertilization potential of mammalian spermatozoa comprises the steps of incubating a sperm sample with extracellular ATP, determining the level of acrosine secretion from the sperm and comparing with the level of acrosine secretion from a control sample of sperm not treated with ATP. A kit for performing the assessment of fertilization potential includes sterile culture medium, sterile, preferably lyophilized ATP, sterile culture tubes and acrosine substrate. A method of inducing the acrosome reaction in sperm taken from an infertile mammal also comprises the incubation of the sperm with extracellular ATP in appropriate culture medium. Sperm treated in this manner may be used in conventional artificial insemination and in vitro fertilization procedures.

19 Claims, 2 Drawing Sheets

METHOD FOR INDUCING THE ACROSOME REACTION IN HUMAN AND ANIMAL SPERMATOZOA

This application is a continuation of U.S. patent application Ser. No. 07/865,605, filed Apr. 9, 1992, now abandoned.

BACKGROUND OF THE INVENTION

1. Field of the Invention

The invention relates to methods for assessing the fertilization potential of mammalian spermatozoa and for inducing the acrosome reaction in such spermatozoa.

2. Description of the Prior Art

It has been known for some time that to be able to fertilize ovulated eggs ejaculated mammalian sperm must reside in the female reproductive tract for several hours; the precise time required varies from one mammal to another. The term "capacitation" was coined to describe this phenomenon. Similarly, sperm removed from the cauda epididymis for in vitro fertilization or for artificial insemination must be incubated under conditions that promote capacitation.

Capacitation has been defined as the process in the female (or in vitro) that prepares the spermatozoon to undergo the acrosome reaction and also quite probably to develop a whiplash or hyperactivated motility that may enhance ability to penetrate the zona pellucida (Yanagimachi, *J. Reproduc. Fertil.*, 23:193–196 (1970)).

The acrosome is a membrane-bound organelle that appears during spermiogenesis as a product of the Golgi complex. It may be considered biochemically analogous to a lysosome. The size and morphology of the acrosome vary considerably from one mammal to another. However, it always occupies the interior region of the sperm head, just above the nucleus and beneath the plasma membrane. Acrosomal membranes underlying the plasma membrane and overlying the nuclear membrane are referred to as the outer and inner acrosomal membrane, respectively.

The acrosome reaction is an exocytotic event involving fusion of sperm plasma and outer acrosomal membranes at many sites, formation of hybrid membrane vesicles that are eventually sloughed from the sperm head, and exposure of acrosomal contents (including a variety of hydrolases, such as hyaluronidase, proteinases, glycosidases, lipases, and phosphatases) and inner acrosomal membrane. Among mammals, only sperm that have undergone the acrosome reaction can penetrate the zona pellucida and, upon reaching the perivitelline space, fuse with egg plasma membrane via plasma membrane overlying the postacrosomal region of the sperm head.

Among the many substances reported to induce mammalian sperm to undergo the acrosome reaction in vitro are serum albumin, β-lactoglobulin, lysolecithin, ionophores, catecholamines, glycosaminoglycans, cyclic nucleotides, steroids, as well as components originating from blood, oviductal fluid, follicular fluid, cumulus cells, oocytes and the zona pellucida. This diversity has led to considerable confusion and controversy about both the nature of the acrosome reaction inducer and the site of the acrosome reaction in vivo. Since only sperm that have undergone the acrosome reaction are capable of penetrating the zona pellucida and fertilizing eggs, these are important issues.

A variety of techniques have been used to detect the acrosome reaction in vitro. Although light microscopy is sufficient to assess the status of the acrosome of some mammalian sperm, in many cases it has been necessary to employ transmission or scanning electron microscopy, or fluorescence microscopy to make an unambiguous assessment.

For an excellent review of the literature on sperm capacitation and the acrosome reaction, see Wassarman, *Ann. Rev. Cell Biol*, 3: 109–142 (1987).

Traditional methods for the evaluation of male infertility consist of taking a history, performing a physical examination and carrying out semen analysis. This last is the most widely used test for the evaluation of the fertility potential of male mammals, with special attention to sperm count, progressive motility and the morphology of the spermatozoa. The number of sperms able to undergo the acrosomal reaction is also ostensibly evaluated. However, on one hand, sperm count, motility and morphology give little information on the ability of the sperm to undergo the acrosomal reaction and to penetrate the egg; on the other, current methods to induce the acrosomal reaction, and therefore test sperm functional parameters, are time consuming and, at best, semiquantitative.

It has been recently suggested that in cases of unexplained infertility in a man judged fertile by standard semen analysis, the fertilizing capacity of spermatozoa could be tested by assaying total seminal acrosine, a trypsin-like enzyme contained in the acrosome which is released during the acrosome reaction and is involved in the fertilization process. The assay technique involves chemical disruption of the acrosome and measurement of the total acrosine content of the sperms. However, there is no firm evidence that the total acrosine content correlates with sperm fertilization ability. The only available test that gives reliable information on the sperm fertilization potential, i.e. the hamster egg penetration test, is not only expensive but also difficult for routine application.

Similarly, no simple, reliable and inexpensive techniques are available for increasing the ability of spermatazoa to undergo the acrosome reaction and, hence, increase the fertilization potential of the sperm. Improved techniques are actively being sought in order to more effectively deal with human and animal male fertility problems.

BRIEF SUMMARY OF THE INVENTION

It is an object of the present invention to provide a simple and rapid technique for determining the fertility potential of mammalian sperm.

It is another object of the present invention to provide a simple laboratory method for the evaluation of the rate of the acrosome reaction in spermatazoa.

It is yet a further object of the present invention to provide a kit for the evaluation of infertility in male mammals which includes all materials necessary to perform a simple test to determine the fertilization potential of a sperm sample.

Still another object of the present invention is to provide a method of "capacitating" mammalian spermatozoa, i.e., enabling the sperm cells to undergo the acrosome reaction and thus be capable of fertilizing an oocyte.

In keeping with these objects and other which will become apparent hereinafter, the invention resides, briefly stated, in a method of testing sperm quality and fertilization potential by taking a sperm sample, washing and resuspending the sperm cells in a culture medium of defined composition, stimulating the cells with extracellular adenosine triphosphate (ATP), and assessing the efficiency of the resulting acrosome reaction by measuring acrosine secretion. Another aspect of the invention comprises a kit for the evaluation of male infertility and the fertilization potential of a sperm sample, said kit including a supply of sterile culture medium, a supply of ATP in suitable form, culture tubes, and a supply of acrosine substrate. An additional aspect of the present invention resides in a method of inducing the acrosome reaction in mammalian spermatozoa by stimulating the sperm cells through incubation in the presence of extracellular ATP.

DETAILED DESCRIPTION OF THE INVENTION

Figure 1:
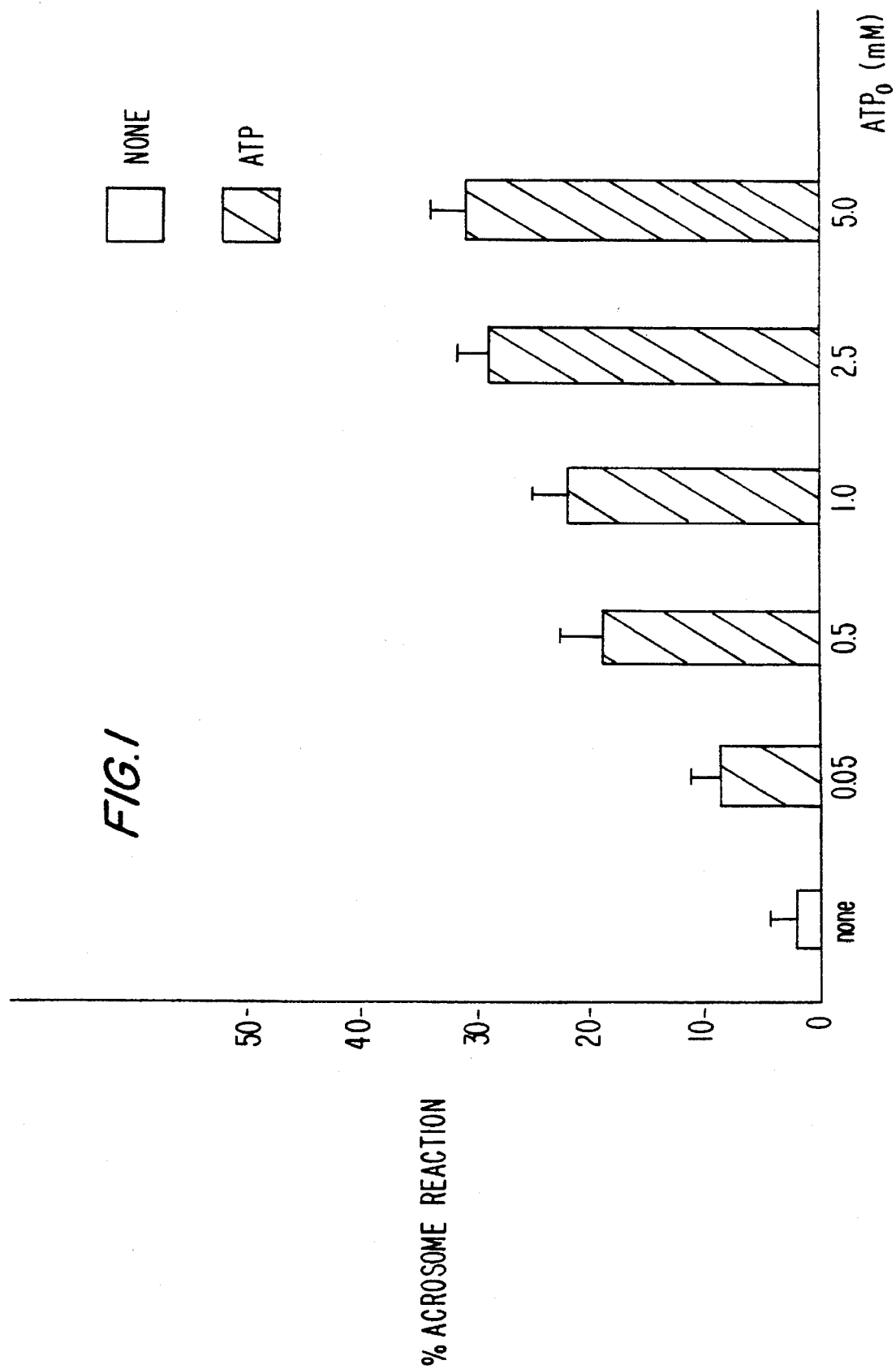
FIG. 1 is a bar graph reflecting the percentage of sperm cells at a concentration of $20 \times 10^6$/ml which underwent the acrosome reaction when incubated in the presence of increasing concentrations of extracellular ATP.

The present invention resides in the unexpected discovery that incubating sperm with extracellular ATP induces the acrosome reaction, i.e., causes the release in the extracellular space of hydrolytic enzymes that allow the sperm to penetrate the zona pellucida surrounding the oocyte. While there are numerous studies disclosed in the literature attempting to correlate sperm ATP content with penetration ability (see, for example, Calamera et al., *Andrologia,* 18:574–580 (1986) and Megory et al., *Arch. Androl.,* 19:243–247 (1987)), these studies deal with the determination of intracellular ATP content and its possible correlation with the ability of the sperm to undergo the acrosome reaction. Furthermore, while other publications have reported the effects of added, extracellular ATP in reactivating the motility of demembranated sperm (i.e., spermatozoa stripped of their outer membranes, usually by treatment with detergent), the aim of those studies was to investigate how the re-addition of ATP, which fuels the activity of the cytoskeletal contractile machinery, regulates the complex phenomenon of sperm cell motility. See, e.g., White et al., *Biol. Reprod.,* 34:183–193 (1986); Yeung, *Int. J. Androl.,* 9:359–370 (1986). To the inventor's knowledge, there have been no published reports of studies dealing with the effect of ATP as an extracellular molecule on sperm capacitation and the acrosome reaction.

It has now been discovered, unexpectedly, that extracellular ATP is a potent activator of human and other mammalian spermatozoa. Several features make this action of extracellular ATP extraordinarily valuable both in terms of fertility assessment techniques and as a tool for enabling sperm to achieve the acrosome reaction:

1. the percentage of acrosome-reacted sperms is similar to that obtained with the best stimulants thus far known;
2. the effects of extracellular ATP are rapid compared to other commonly used stimulants;
3. at optimal concentrations and in contrast to some powerful activators, such as the calcium ionophores, extracellular ATP has no toxic effect on sperm motility and viability; and
4. spermatozoa treated with extracellular ATP have a very high success rate in the standard hamster egg fertilization test.

The first aspect of the present invention is a method of assessing the fertilizing potential of a mammalian sperm sample. In a preferred embodiment, the method comprises the steps of:

a) taking a semen specimen from a mammalian subject and diluting it with an appropriate culture medium;

b) separating the spermatozoa from the seminal plasma, e.g., by washing;

c) resuspending the sperm in culture medium;

d) taking a first sample of the resuspended sperm, for example about 1 ml thereof, and diluting it with culture medium containing sufficient dissolved ATP to give a final ATP concentration in said first sample of about 0.5 to about 10.0 mM, and preferably from about 1 to about 2.5 mM;

e) diluting a second sample of the resuspended sperm with an equivalent volume of non-ATP containing culture medium, said second sample to be used as a control;

f) incubating both samples at about 30°–40° C.; and g) centrifuging the incubated sperm samples and measuring the acrosine content in the supernatant spectrophotometrically.

Comparison of the acrosine concentration in the respective supernatants of the ATP-treated and control sperm samples gives a reliable indication of the sperm cells' ability to undergo the acrosome reaction, and hence, an indication of their fertilization potential.

The first aspect of the invention is not limited to the specific steps set forth above in the preferred embodiment. The invention comprehends any technique or procedure which may be adapted or conceived by those skilled in the art which includes the steps of treating mammalian sperm with extracellular or exogenous ATP to induce the acrosome reaction and subsequently quantitatively determining acrosine secretion from the sperm cells.

A second aspect of the present invention is a kit for the evaluation of the fertilization potential of mammalian sperm in accordance with the above-described method. The kit includes (a) a supply of sterile culture medium; (b) a supply of sterile lyophilized ATP; (c) a set of sterile culture tubes; and (d) a supply of acrosine substrate to be used in assaying for acrosine in the supernatants of the sperm samples by conventional means.

Both the method of the present invention for assessing the fertilization potential of mammalian sperm and the kit provided for the same purpose enable simple, rapid, accurate and inexpensive techniques for evaluating human infertility problems, assessing the value of animal sperm in commercial fertilization processes, and other applications where a quick and accurate determination of fertilization potential is required.

In a further aspect of the present invention, extracellular ATP is added to whole (non-demembranated) sperm to enable said sperm to undergo the acrosome reaction and, hence, be capable of fertilization. In accordance with this aspect of the invention, a semen specimen is taken from an infertile or less fertile male and treated with extracellular ATP, preferably in lyophilized form, in the same manner as described previously in connection with the technique for assessing fertilization potential. The sperm is incubated with sufficient ATP-containing culture medium so that the total concentration of ATP is from about 0.5 to about 10 mM, and preferably from about 1.0 to about 2.5 mM. The sperm capacitated by this method may be used in any conventional artificial insemination or in vitro fertilization procedures.

The following examples provide a detailed illustration of the method of the present invention for determining the fertilization potential of a sperm sample, and, thus, the fertility level of a male mammal. The examples are not intended, however, to be limiting in any sense or to provide specific procedures, materials, reagents or apparatus which must be utilized exclusively to practice the present invention.

EXAMPLE 1

A semen sample is obtained from a mammalian donor, placed into a sterile plastic tube and allowed to liquefy at room temperature for about 30 minutes. The sample is analyzed for semen volume and pH and sperm concentration, motility, viability and morphology. The semen is diluted 1:4 v/v with a culture medium containing 95 mM NaCl, 4.8 mM KCl, 1.7 mM $CaCl_2$, 1.2 mM $KH_2PO_4$, 1.2 mM $MgSO_4$, 20 mM N-2-hydroxyethylpiperazine-N-2-ethanesulphonic acid (HEPES), 25 mM $NaHCO_3$, 5.6 mM fructose, 0.25 mM Na pyruvate, 3.7 ml/L of sodium lactate syrup (60%), $10^4$ IU/ml penicillin and 10 mg/ml streptomycin. Spermatozoa are then separated from seminal plasma by centrifugation at 800 xg for 10 minutes and resuspended at $20\times10^6$/ml.

Lyophilized ATP is dissolved in 1 ml of culture medium (ATP is provided in aliquots of 3.5 mg, a quantity sufficient to give a concentration of 5 mM when dissolved in 1 ml of culture medium). One ml of the sperm suspension is diluted 1:1 v/v with the ATP-containing culture medium to give a final ATP concentration of 2.5 mM and incubated for 1 hour at 37° C. A parallel sample of spermatozoa is diluted 1:1 v/v with ATP-free culture medium (control sample) and also incubated for 1 hour at 37° C. At the end of this incubation the sperm samples are centrifuged at 800 xg and acrosine content in the supernatants measured spectrophotometrically. Acrosine concentration in the supernatant gives a reliable indication of the acrosome reaction and therefore of the fertilization potential of the sperms.

EXAMPLE 2

The validity of the method of the present invention was demonstrated by following the procedure of Example 1 but incubating five sperm samples taken from the original semen specimen, each containing sperm at a concentration of $20\times10^6$/ml, for 1 hour in the presence of respective concentrations of extracellular ATP ranging from 0.05 mM to 5.0 mM. A sixth sperm sample was used as a control and was incubated without any added ATP. After incubation, the percentage of sperm undergoing the acrosome reaction in the total sperm population in each sample was determined.

As shown in FIG. 1, there was a direct correlation between the extracellular ATP concentration in each sperm sample and the percentage of sperm undergoing the acrosome reaction, with only a few percent of the sperm undergoing the reaction in the control sample and about 30% or more undergoing the acrosome reaction in the samples incubated with ATP concentrations of 2.5 mM and 5.0 mM, respectively.

EXAMPLE 3

Figure 2:
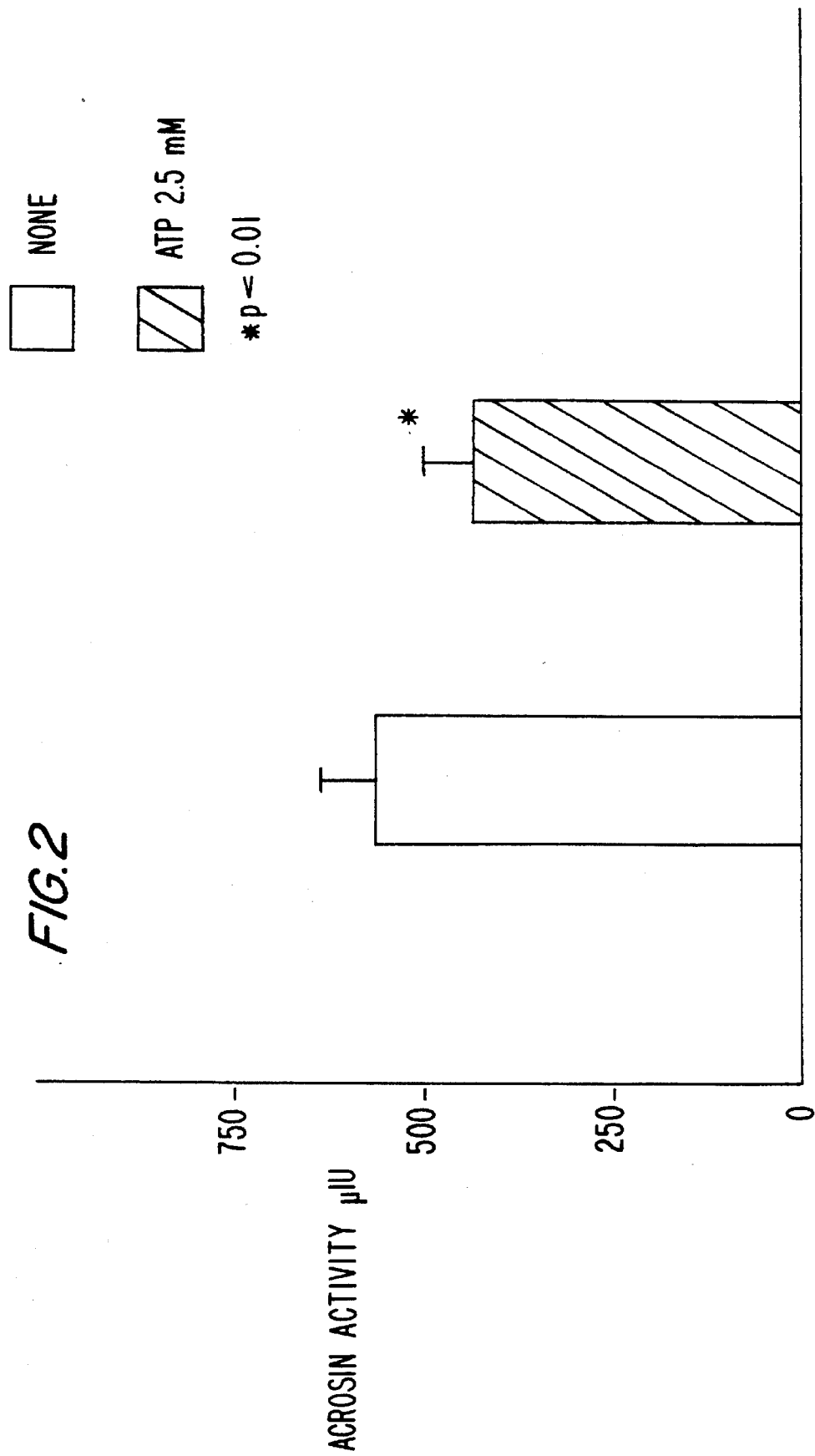
FIG. 2 is a bar graph comparing total acrosine activity in resting human sperm cells and in sperm cells after induction of the acrosome reaction with 2.5 mM extracellular ATP.

To further confirm the validity of the present method, total acrosine content in resting human sperms and in samples of the same sperm after incubation with 2.5 mM extracellular ATP were compared. As illustrated in FIG. 2, the acrosine content in the sperms treated with ATP was significantly lower than in the resting sperms, indicating that substantial secretion of acrosine from the sperms was stimulated by incubation with extracellular ATP.

It has thus been shown that there are provided methods which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the following claims.

We claim:

1. A method of assessing the fertilization potential of sperm from a mammalian subject, comprising the steps of:
   a) obtaining a 0.2 to 1.0 ml sample of the sperm;
   b) without demembranating the sperm or treating it to increase sperm cell membrane permeability, incubating the sperm sample in a suitable culture medium with sufficient extracellular ATP to yield a final ATP concentration of 0.5 to 10.0 mM;
   c) determining the level of acrosin secretion from the ATP-treated sperm by spectrophotometric measurement; and
   d) comparing spectrophotometrically the respective levels of acrosin secretion into culture medium by (i) the ATP-treated sperm and (ii) a control sample of untreated sperm taken from the same subject whereby the magnitude of the difference in acrosin secretion levels between the ATP-treated sperm and the control sample correlates to the fertilization potential of the subject's sperm.

2. A method of assessing the fertilization potential of sperm from a mammalian subject, comprising the steps of:
   a) taking a semen specimen from the subject and diluting said specimen with a suitable culture medium;
   b) washing the spermatozoa in the specimen free of seminal plasma without demembranating the spermatozoa or treating them to increase their permeability;
   c) resuspending the spermatozoa in culture medium;
   d) diluting a first sample of the resuspended spermatozoa with culture medium containing sufficient dissolved ATP to give a final ATP concentration in said first sample of 0.5 to 10.0 mM;
   e) taking a second sample of the resuspended spermatozoa and diluting said sample with a non-ATP containing culture medium;
   f) incubating both of said first and second samples at 30°–40° C.;
   g) centrifuging the incubated sperm samples and measuring the acrosin contents thereof; and
   h) comparing the acrosin contents of the first and second samples by spectrophotometric measurement whereby the magnitude of the difference in acrosin secretion levels between the first and second sperm samples correlates to fertilization potential of the subject's sperm.

3. A method according to claim 2 wherein the ATP is lyophilized before being dissolved in the culture medium.

4. A method according to claim 2 wherein the final ATP concentration in said first sample is 1.0 to 2.5 mM.

5. A method according to claim 4 wherein the final ATP concentration is 2.5 mM.

6. A method according to claim 1 wherein the final ATP concentration is 5.0 mM.

7. A method according to claim 2 wherein the samples are incubated at 37° C.

8. A method according to claim 2 wherein the concentration of spermatozoa resuspended in the culture medium is about $20 \times 10^6$/ml.

9. A method according to claim 2 wherein the subject is human.

10. A method according to claim 2 wherein the subject is a non-human mammal.

11. A kit for the evaluation of the fertilization potential of mammalian sperm comprising:

a) a supply of sterile culture medium;

b) a supply of sterile ATP;

c) a set of sterile culture tubes; and d) a supply of acrosine substrate suitable for use in assaying for acrosine.

12. A kit according to claim 11 wherein the ATP is lyophilized.

13. A method of inducing mammalian sperm to undergo the acrosome reaction, comprising the steps of:

a) taking a semen specimen from an infertile male subject;

b) separating the spermatozoa from the seminal plasma; and c) treating the spermatozoa with extracellular ATP in culture medium, whereupon the spermatozoa may be used in artificial insemination or in vitro fertilization procedures.

14. A method according to claim 13 wherein the subject is human.

15. A method according to claim 13 wherein the subject is a non-human mammal,

16. A method according to claim 13 wherein the spermatozoa are incubated with ATP dissolved in culture medium.

17. A method according to claim 16 wherein the concentration of ATP in the culture medium in which the spermatozoa are incubated is from 0.5 to 10 mM.

18. A method according to claim 17 wherein the concentration of ATP is from 1.0 to about 2.5 mM.

19. A method according to claim 13 wherein the ATP is lyophilized before being added to the culture medium.

* * * * *